(12) United States Patent
Pei et al.

(10) Patent No.: US 7,749,766 B2
(45) Date of Patent: Jul. 6, 2010

(54) BILIRUBIN SENSOR

(75) Inventors: Jianhong Pei, Boxborough, MA (US); Mary M. Lauro, N. Billerica, MA (US); Chung Chang Young, Weston, MA (US)

(73) Assignee: Nova Biomedical Corporation, Waltham, MA (US)

( * ) Notice: Subject to any disclaimer, the term of this patent is extended or adjusted under 35 U.S.C. 154(b) by 846 days.

(21) Appl. No.: 11/622,564

(22) Filed: Jan. 12, 2007

(65) Prior Publication Data
US 2008/0169206 A1 Jul. 17, 2008

(51) Int. Cl.
*G01N 33/72* (2006.01)
*G01N 27/26* (2006.01)

(52) U.S. Cl. .............................. 436/97; 436/63; 436/70; 436/149; 436/150; 436/151; 436/177; 422/68.1; 422/82.01; 422/82.02; 204/400; 204/403.01; 204/403.14; 204/412; 205/780.5

(58) Field of Classification Search .................... 436/63, 436/70, 97, 149, 150, 151, 175, 177; 422/68.1, 422/82.01, 82.02; 204/400, 403.01, 403.02, 204/403.03, 403.04, 403.14, 411, 412; 205/780.5
See application file for complete search history.

(56) References Cited

U.S. PATENT DOCUMENTS

| | | | |
|---|---|---|---|
| 4,338,095 A | | 7/1982 | Wu |
| 4,985,360 A | * | 1/1991 | Takahashi et al. ............. 435/25 |
| 5,149,272 A | | 9/1992 | Wu et al. |
| 5,278,073 A | | 1/1994 | Grandjean |
| 5,563,072 A | | 10/1996 | Tokuda et al. |
| 6,326,208 B1 | | 12/2001 | Denney |
| 6,882,873 B2 | | 4/2005 | Samuels et al. |
| 2004/0014023 A1 | * | 1/2004 | Meserol et al. ................ 435/2 |
| 2007/0080073 A1 | * | 4/2007 | Wu et al. .................. 205/777.5 |
| 2007/0131548 A1 | * | 6/2007 | Winarta et al. ......... 204/403.02 |
| 2007/0131549 A1 | * | 6/2007 | Cai et al. ............... 204/403.02 |
| 2007/0131565 A1 | * | 6/2007 | Fujiwara et al. .......... 205/777.5 |
| 2007/0281321 A1 | * | 12/2007 | Nagale et al. ................ 435/7.1 |
| 2008/0302659 A1 | * | 12/2008 | Sheppard et al. ....... 204/403.01 |

FOREIGN PATENT DOCUMENTS

EP 320095 * 6/1989

OTHER PUBLICATIONS

Ogawa, Jun et al., "Bilirubin Dehydrogenase, an Enzyme in *Aspergilus ochraceus* IB-3 Useful for Diagnostic Measurement of Bilirubin," Biosci. Biotechnol. Biochem., 66 (11), pp. 2376-2381, 2002.

(Continued)

*Primary Examiner*—Maureen M Wallenhorst
(74) *Attorney, Agent, or Firm*—Robert R. Deleault, Esq.; Mesmer & Deleault, PLLC

(57) ABSTRACT

A bilirubin sensor has a working electrode with a first chemical matrix disposed thereon that contains a binder, a substrate electrode with a second chemical matrix dispose thereon that contains a binder and a chemical agent that consumes bilirubin, a reference electrode, a sample chamber containing the working electrode, the substrate electrode and the reference electrode, and a method of measuring bilirubin in a body fluid.

25 Claims, 7 Drawing Sheets

OTHER PUBLICATIONS

Martinek, R. G., "Improved Micro-method for Determination of Serum Bilirubin," Clinica Chimica Acta, 13, pp. 161-170, (1966).

Walters, Martha I. et al., "An Ultramicromethod for the Determination of Conjugated and Total Bilirubin in Serum or Plasma," Microchemical Journal, 15, pp. 231-243, (1970).

Ahlfors, Charles E., "Measurement of Plasma Unbound Unconjugated Bilirubin," Analytical Biochemistry, 279, pp. 130-135, (2000).

Klemm, Johanna, et al., "An Enzymic Method for the Determination of Bilirubin Using an Oxygen Electrode, "Electroanalysis, 12, No. 4, pp. 292-295, (2000).

Shoham, Benjamin et al., "A bilirubin biosensor based on a multilayer network enzyme electrode," Biosensor & Bioelectronics, 10, pp. 341-352, (1995).

O'Leary, Niall et al., "A robust procedure for the automated measurement of total serum bilirubin using potassium ferricyanide," Ann. Clin. Biochem., 30, pp. 175-179, (1993).

Lo, Donald H. et al., "Assessment of the Fundamental Accuracy of the Jendrassik-Grof Total and Direct Bilirubin Assays," Clinical Chemistry, 29 (1), pp. 31-36, (1983).

Wu, T. W. et al., "Biliprotein in the Adult Icteric Serum—Demonstrated by Extension of the Alkaline Methanolysis Procedure," Clinical Chemistry, 28 (12), pp. 2398-2404, (1982).

Dappen, Glen M. et al., "A Diazo-Based Dry Film for Determination of Total Bilirubin in Serum," Clinical Chemistry, 29 (1), pp. 37-41, (1983).

* cited by examiner

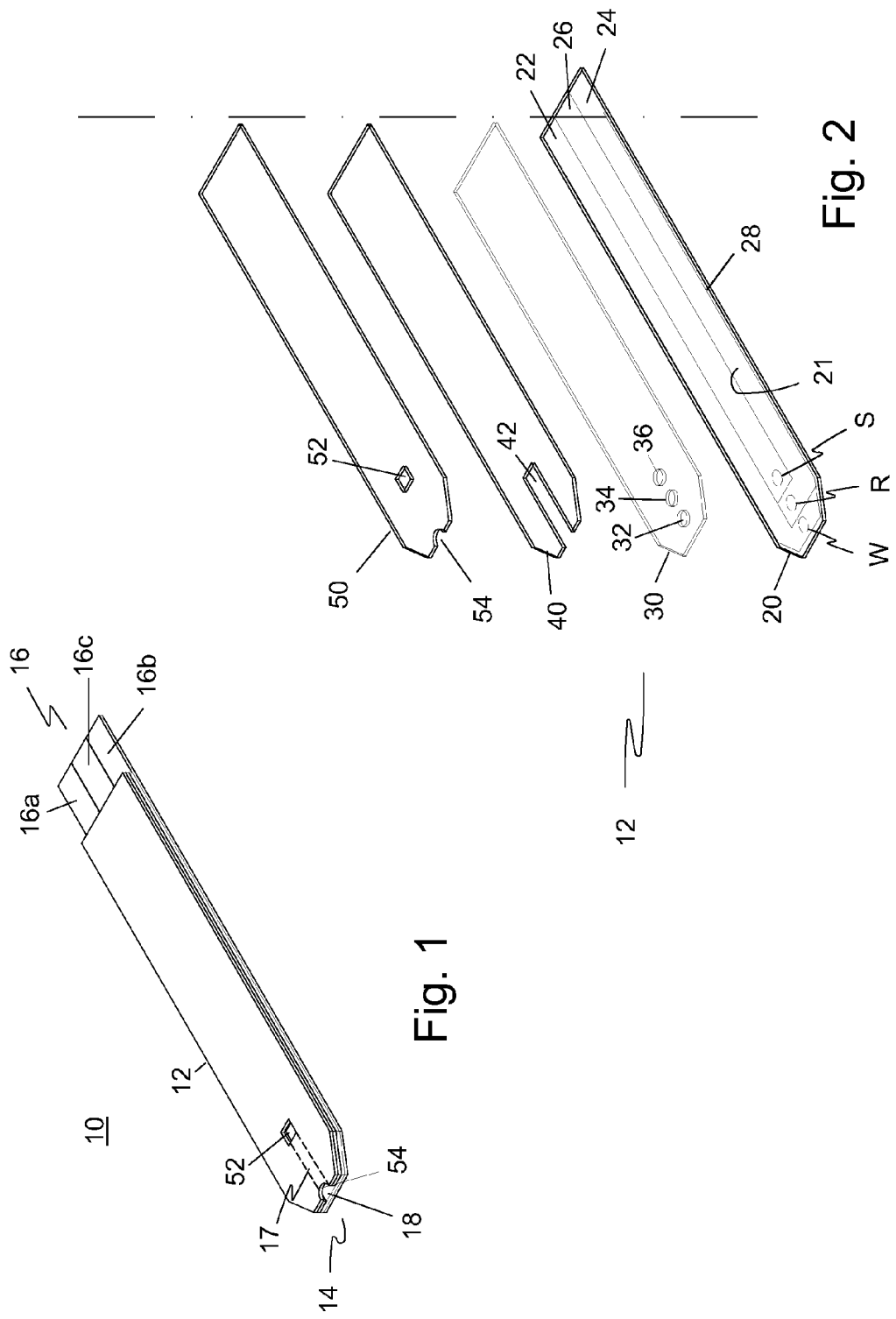

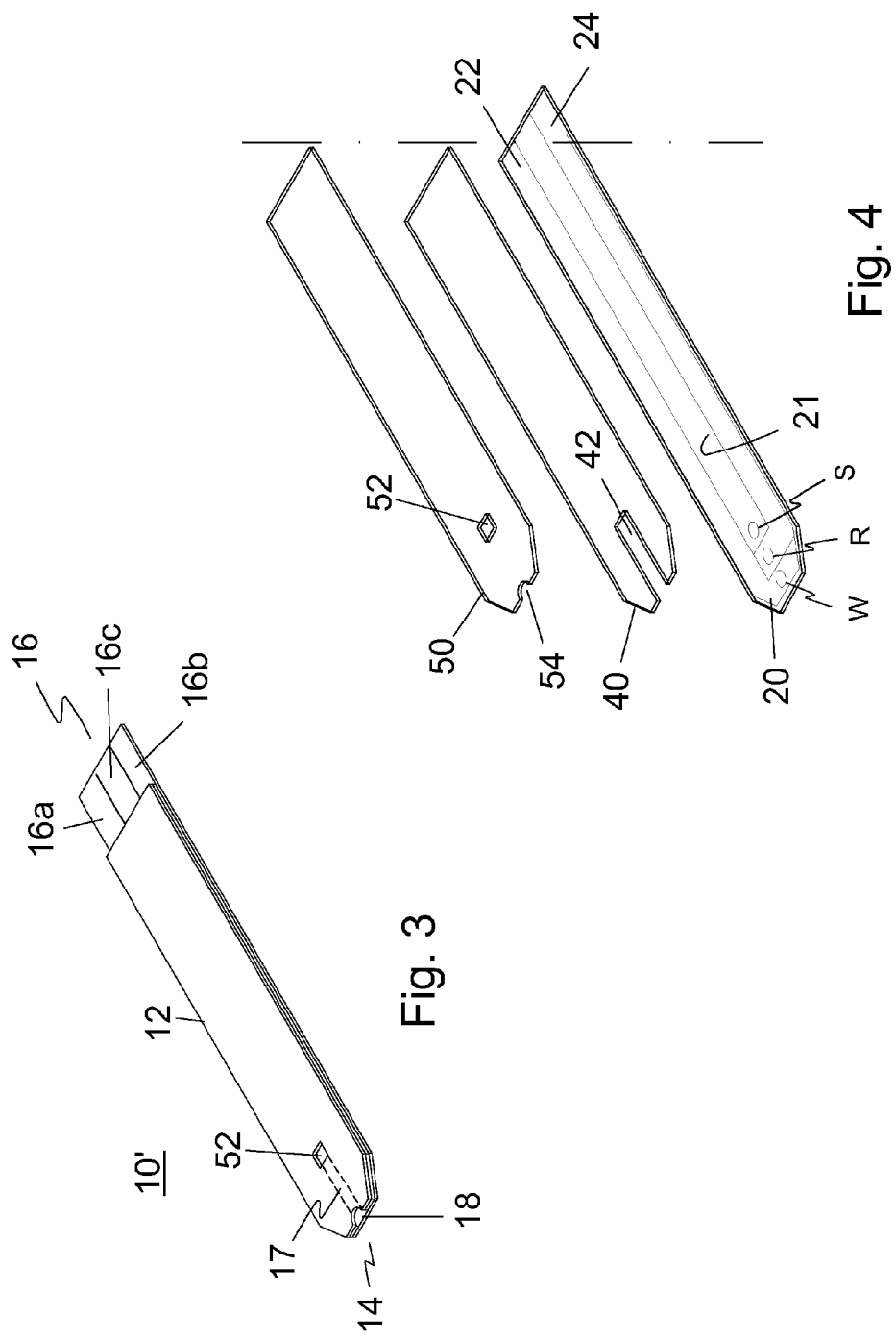

BILIRUBIN SENSOR

BACKGROUND OF THE INVENTION

1. Field of the Invention

The present invention relates generally to electrochemical sensors that can be used for quantification of a specific component or analyte in a liquid sample. Particularly, the present invention relates to an electrochemical-based sensor for measuring bilirubin in biological fluids.

2. Description of the Prior Art

Bilirubin is the main bile pigment that is formed from the breakdown of heme from red blood cells. The broken-down heme travels to the liver, where it is secreted into the bile by the liver. It is estimated that approximately 200 to 300 milligrams of bilirubin and its derivatives are formed each day in a normal human adult by degradation of hemoglobin within the liver, spleen, and bone marrow. Normally, a small amount of bilirubin circulates in the blood. Serum bilirubin is considered a true test of liver function as it reflects the liver's ability to take up, process, and secrete bilirubin into the bile.

Two fractions of bilirubin are present in blood serum. One is free or non-conjugated bilirubin and the other conjugated bilirubin since it has become conjugated with glucuronic acid and rendered water-soluble. The diagnostic significance of bilirubin is well established. An excessive amount of bilirubin within the human body, referred to as jaundice, is recognized as evidence of a variety of disease conditions, particularly diseases of the liver. In an adult, bilirubin could be excreted from the body by way of the bile fluids. In a fetus, bilirubin can easily cross the placenta and be removed through the mother's liver. Newborn infants and especially prematurel infants, however, are particularly susceptible to hyperbilirubinemia. Hyperbilirubinemia is defined as an abnormally high level of bilirubin in the blood, manifested by jaundice, anorexia, and malaise, occurring in association with liver disease and certain hemolytic anemias. Because an infant's liver is not fully functioning for the first few weeks after birth, bilirubin may accumulate above normal adult levels, which "stains" infant's skin leading to jaundice. Clinically, untreated jaundice in neonates can lead to impaired learning ability, mental retardation, cerebral palsy, seizures, deafness, or even death.

There are several methods used to determine bilirubin concentration. The leading method is the so-called diazo method, which measures the purplish-red color of azobilirubin formed by the reaction of bilirubin with a diazo compound. There are numerous versions of the diazo method, differing in the reaction conditions and reagent composition. The method according to Jendrassik and Gróf has been recommended by the National Committee for Clinical Laboratory Standard (NCCLS) as the procedure of choice for total bilirubin measurement. There are, however, disadvantages associated with this method. For example, the reagent solutions for the Jendrassik/Gróf method can be used for only about 5 days after their preparation, and the measured values are affected by L-ascorbic acid and hemoglobin, which are present in a sample.

The total bilirubin level in bodily fluids has been measured by direct spectrophotometric estimation at 454 nm with correction at 540 nm. This direct spectrophotometric measurement has been improved by making observations before and after the destruction of bilirubin with the enzyme bilirubin oxidase. O'Leary et.al (Ann. Clin. Biochem., 30:175-179, (1993)) describes a two-step method based on the measurement of absorbance of bilirubin itself at about 480 nm, followed by measurement of absorbance at 480 nm after destruction of the bilirubin with ferricyanide. This method is limited due to the use of the 480 nm wavelengths of detection. At this wavelength, highly lipemic or hemolyzed sera may cause the absorbance, and a false result may be produced.

U.S. Pat. No. 6,326,208 (2001, Denney) discloses an assay for measuring total and direct bilirubin colorimetrically that includes the use of a first or a second reagent, respectively. For total biliruben, the first reagent includes a solvent in which the bilirubin and the proteins are soluble, an acid, and a promoter for speeding up the oxidation of the bilirubin and the formation of a chromophore that is detectable in the near-infrared region of the spectrum. Useful promoters are nitrite ion, cupric ion and ferricyanide ion. For direct bilirubin, the second reagent includes an aqueous component containing an acid for dissolving both the serum or plasma proteins and the conjugated bilirubin of the sample, and an oxidant for promoting the oxidation of the conjugated bilirubin while promoting very little oxidation of unconjugated bilirubin. The oxidant should have a low single electrode potential between 0.34 and 0.78 volts. Useful oxidants are cupric ion, ferric ion and ferricyanide ion.

U.S. Pat. No. 5,563,072 (1996, Tokuda et al.) discloses a method of measuring direct bilirubin calorimetrically that includes using bilirubin oxidase or a chemical oxidizing agent of vanadic ions, manganese (III) ions, ferricyanide ions or copper ions. Another method includes additionally using a reaction inhibitor that is a water-soluble high polymer or a nonionic surfactant having a HLB value of 15 or more.

Yet another method involves the use of a dry film for determination of serum bilirubin, which is based on the observation that bilirubin interacts with certain cationic polymers (mordants) giving a unique spectral change. A transparent support is coated with a buffered gelatin-mordant layer and an isotropically porous polymer spreading layer. The spreading layer contains all of the necessary components (diazonium salt, accelerator, surfactant) for the quantification of bilirubin. The buffered gelatin-mordant layer maintains the pH of the dry film, minimizes the dependence of spot size on protein concentration, and increases the sensitivity of the dry film. The dry film, however, is only stable for 4 weeks at room temperature and cannot be used for whole blood analysis.

Therefore, what is needed is a bilirubin sensor that is usable with whole blood. What is also needed is a bilirubin sensor that is capable of performing an accurate and sensitive analysis of the concentration of bilirubin in a small volume of biological sample. What is further needed is a bilirubin sensor that is disposable.

SUMMARY OF THE INVENTION

It is an object of the present invention to provide a bilirubin sensor capable of measuring the bilirubin concentration in a small volume of bodily fluid. It is another object of the present invention to provide a bilirubin sensor that is usable without routine maintenance. It is a further object for the present invention to provide a bilirubin sensor that measures bilirubin in a fluid sample electrochemically. It is still another object of the present invention to provide a bilirubin sensor that includes an interference-correcting electrode to minimize the interference caused by the presence of other oxidizable components in the sample fluid. It is yet another object of the present invention to provide a disposable bilirubin sensor. It is still a further object of the present invention to provide a disposable bilirubin sensor that is capable of measuring the bilirubin concentration in biological fluid including blood obtained by lancing the finger of the user. It is another object of the present invention to provide a disposable bilirubin sensor for measuring bilirubin concentration in a small volume of whole blood.

The present invention achieves these and other objectives by providing a disposable bilirubin sensor having a working electrode, a substrate electrode and a reference electrode disposed within a sample chamber configured for receiving a liquid sample. The working electrode includes an electrical conductor with a first reagent matrix disposed thereon that contains a binder. The substrate electrode includes an electrical conductor with a second reagent matrix disposed thereon that contains a binder and a chemical agent that consumes bilirubin to prevent the bilirubin from being oxidized at the surface of the substrate electrode by a voltage that is applied to the bilirubin sensor. The first reagent matrix and the second reagent matrix can also each contain a whole blood filtering component. The reference electrode includes an electrical conductor and a reference reagent matrix disposed thereon. The reference reagent matrix may be any reference material including, but not limited to, a binder, silver-silver chloride or other reference electrode materials.

Bilirubin is a reductant that is easily oxidized at an electrode surface if a sufficient positive potential is applied at the electrode. Bilirubin is also easily oxidized by a chemically oxidizing reagent such as ferricyanide compounds, cupric compounds, nitrite compounds, Ruthenium compounds, osmium compounds, and the like. When using redox mediators to oxidize bilirubin, the redox mediator changes from its oxidation form to its reduction form (for example from $Fe(CN)_6^{3-}$ to $Fe(CN)_6^{4-}$ for ferricyanide compounds). The reduced redox mediator (such as $Fe(CN)_6^{4-}$) can be re-oxidized electrochemically to its oxidation form (such as $Fe(CN)_6^{3-}$) at the electrode surface when a positive potential is applied to the electrodes. The resulting current is related to the bilirubin concentration.

Unfortunately, other species in a sample fluid such as a body fluid are also capable of undergoing a similar reaction and causing a false determination of bilirubin concentration. These other oxidizable species include ascorbic acid, uric acid, acetaminophen, and the like. The present invention provides an apparatus and a method for a more accurate electrochemical measurement of bilirubin concentration in biological fluid samples in the presence of these other interfering species. An important feature of the present invention that accomplishes this more accurate measurement is the substrate electrode. The substrate electrode is loaded with a chemical agent that consumes bilirubin to prevent it from being oxidized by the chemically oxidizing reagent. The chemical agent is preferably a bilirubin sensitive enzyme and, more preferably, bilirubin oxidase.

The resulting current from the working electrode is related to all the reductants in the sample fluid and the current from the substrate electrode is related to all the reductants in the sample fluid except bilirubin. The differential current between the working electrode and the substrate electrode is related to the concentration of bilirubin in the sample fluid. Therefore, use of a working electrode and a substrate electrode provides a more accurate measurement and correlation to the concentration of bilirubin. In addition, because the current arising from the reductants except bilirubin is measured, any variation in the concentration of these oxidizable species from sample to sample is nullified and, thus, provides a more accurate measurement of bilirubin in the sample fluid.

In addition to the concentration of bilirubin, the differential current is also influenced by hematocrit when the fluid samples are blood samples. The effect of hematocrit can be eliminated by measuring the impedance (Imp) or resistance (R) of the blood samples. For purposes of the following equations, impedance and resistance is used interchangeably since the measurement value for the impedance or resistance is Ohms. Hematocrit effect can be corrected and eliminated using the following equations:

$$H=(a_1)(R^2)+(a_2)(R)+a_3 \qquad (1)$$

where R is the resistance value measured in Ohms, H is hematocrit value, and $a_1$, $a_2$ and $a_3$ are constants.

The hematocrit value is then used to mathematically correct the bilirubin concentration measured using the above described sensor. The following equation represents the calculation preformed using the calculated hematocrit level from equation (1):

$$C_{corr}=(C_{mea})((b)(H^2)+(c)(H)+d) \qquad (2)$$

where $C_{corr}$ is the corrected analytical concentration $C_{mea}$ is the measured analytical concentration b, c, and d are constants H is the hematocrit level calculated from equation (1)

The constant values "a" through "d" above are especially determined and dependent on several factors such as the arrangement of the electrodes, the formulations of the chemical reagents, the surface area of the electrodes, and the ratio of the surface areas of the electrodes. Once these factors are set, numerical analysis is performed on the test data obtained from predefined sample fluid standards using a plurality of sensors having these preset factors in common. The correction can also be done by using the ohmic value without converting the ohmic value to hematocrit by simply substituting equation (1) into equation (2) and creating an algorithm that uses the ohmic value to correct for the effect of hematocrit in the sample fluid.

All of the advantages of the present invention will be made clearer upon review of the detailed description, drawings and appended claims.

BRIEF DESCRIPTION OF THE DRAWINGS

FIG. 1 is a perspective view of one embodiment of the present invention showing the test strip.

FIG. 2 is an exploded view of the embodiment in FIG. 1 showing the four component layers of the test strip.

FIG. 3 is a perspective view of another embodiment of the present invention showing the test strip.

FIG. 4 is an exploded view of the embodiment in FIG. 3 showing the three component layers of the test strip.

DETAILED DESCRIPTION OF THE PREFERRED EMBODIMENT

Figure 5:
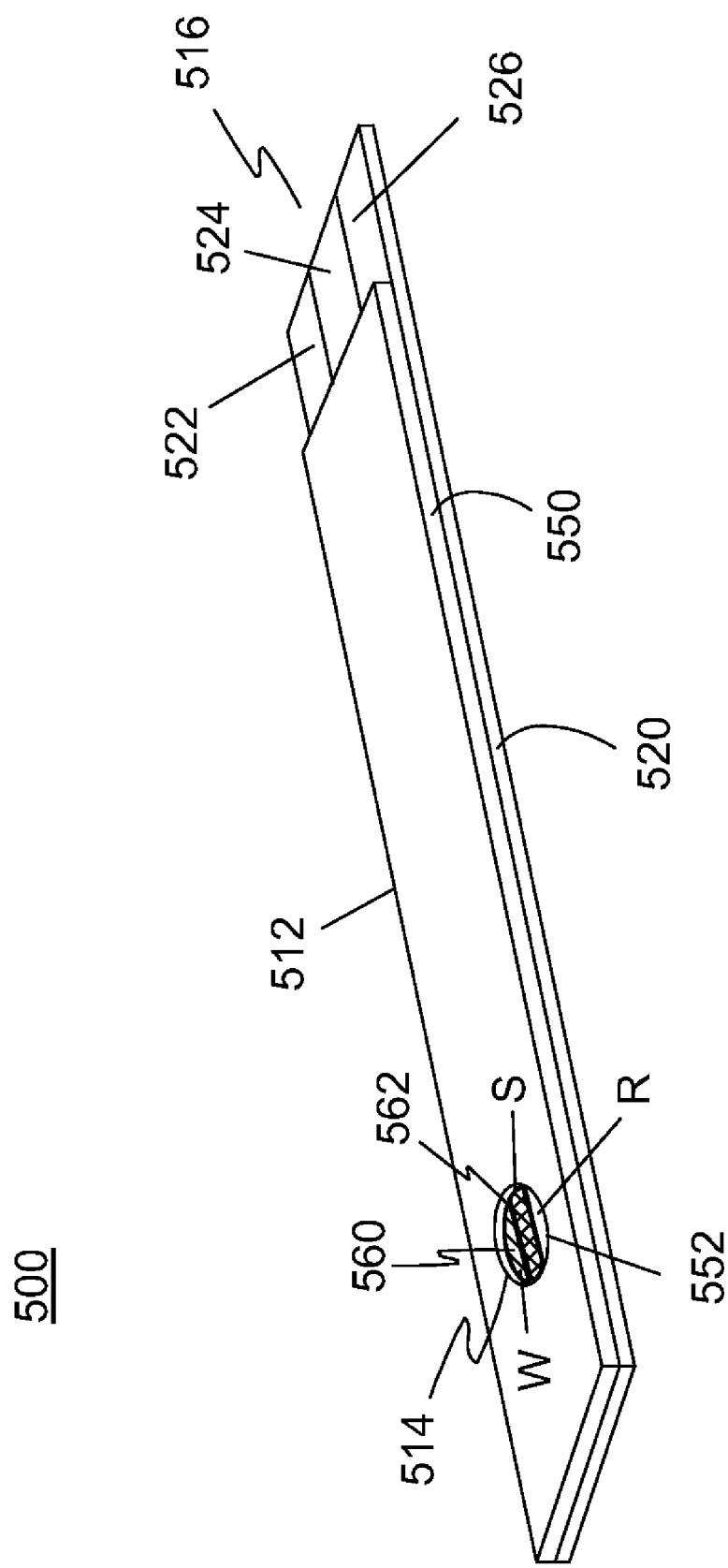
FIG. 5 is a perspective view of another embodiment of the present invention.

The preferred embodiment(s) of the present invention is illustrated in FIGS. 1-9. FIG. 1 illustrates one embodiment of the present invention. The bilirubin sensor 10 has a laminated body 12, a fluid sampling end 14, an electrical contact end 16, and a vent opening 52. Fluid sampling end 14 includes a sample chamber 17 between a sample inlet 18 and vent opening 52. Electrical contact end 16 has three discrete conductive contacts 16a, 16b and 16c.

Turning now to FIG. 2, laminated body 12 includes a base layer 20, a reagent holding layer 30, a channel forming layer 40, and a cover 50. All layers of laminated body 12 are made of a dielectric material, preferably plastic. Examples of a preferred dielectric material are polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene and polystyrene.

Base layer 20 has a conductive layer 21 on which is delineated three conductive paths 22, 24 and 26. The conductive paths 22, 24, 26 may be formed by scribing or scoring conductive layer 21. In the alternative, base layer 20 may be a dielectric material on which conductive paths 22, 24, 26 are silk screened.

Scribing or scoring of conductive layer 21 may be done by mechanically scribing the conductive layer 21 sufficiently to create the three independent conductive paths 22, 24, 26. The preferred scribing or scoring method of the present invention is done by using a carbon dioxide laser, a YAG laser or an eximer laser. Conductive layer 21 may be made of any electrically conductive material such as, for example, gold, tin oxide/gold, palladium, other noble metals or their oxides, or carbon film compositions. The preferred electrically conductive material is gold or tin oxide/gold. An additional scoring line 28 (enlarged and not to scale; for illustrative purposes only) may be made along the outer edge of base layer 20 in order to avoid possible static problems that could give rise to a noisy signal. It should be understood, however, that scoring line 28 is not necessary to the functionality of sensor 10. Conductive layer 21 may be made of any electrically conductive material such as, for example, gold, tin oxide/gold, palladium, other noble metals or their oxides, or carbon film compositions. The preferred material for the base layer 20 is gold coated polyester film.

Reagent holding layer 30 has a first electrode opening 32 which exposes a portion of first conductive path 22, a second electrode opening 34 which exposes a portion of second conductive path 24, and a third electrode opening 36 which exposes a portion of third conductive path 26. Reagent holding layer 30 is made of a plastic material, preferably a medical grade, one-sided adhesive tape available from Adhesive Research, Inc., of Glen Rock, Pa. or Global Instrument Corporation (GIC) (Taiwan). Acceptable thicknesses of the tape for use in the present invention are in the range of about 0.001 in. (0.025 mm) to about 0.005 in. (0.13 mm). The preferred thickness is about 0.003 in. (0.075 mm). It should be understood that the use of a tape is not required. Reagent holding layer 30 may be made from a plastic sheet and may be coated with a pressure sensitive adhesive, a photopolymer, ultrasonically-bonded to base layer 20, or silk-screened onto the base layer 20 to achieve the same results as using the polyester tape mentioned.

The three electrode openings 32, 34 and 36 define electrode wells W, R and S, respectively, and hold chemical reagents forming a working electrode, a reference electrode, and a substrate electrode. Preferably, electrode well W is loaded with a chemically oxidizing reagent and at least a polymer binder. Substrate electrode well S is loaded with a similar chemistry to electrode well W, but with the addition of a chemical agent that consumes bilirubin before the bilirubin can be oxidized by the mediator at the surface of the electrode by a voltage that is applied to the bilirubin sensor during use. The term "consuming bilirubin" means that the bilirubin is removed by the oxidase so that it cannot be oxidized by the mediator when voltage is applied to the electrode. Preferably, the chemical agent is a bilirubin sensitive enzyme and, more preferably, it is bilirubin oxidase. One or more chemical components such as additional polymers, stabilizers, and bulking agents may be optionally included in the reagent matrix. A reference reagent matrix is loaded in electrode well R.

Preferably, the reference matrix contains at least a chemically oxidizing reagent such as a reduced form of a redox mediator, an oxidized form of redox mediator, or a mixture of a reduced and an oxidized form of a redox mediator. For example, potassium ferricyanide, or potassium ferrocyanide, or a mixture of potassium ferricyanide and potassium ferrocyanide may be loaded to make the reference electrode function when using the preferred conductive coating material. The mixture of potassium ferricyanide and potassium ferrocyanide may be prepared such that the potassium ferricyanide concentration is in the range of up to about 10%, while the potassium ferrocyanide concentration is in the range of up to about 5%. In the alternative, the reference electrode (electrode well R) may be loaded with an Ag/AgCl layer (e.g., by applying Ag/AgCl ink or by sputter-coating (a) a Ag layer followed by chloridizing the Ag or (b) a Ag/AgCl layer) or other reference electrode materials that do not require a redox mediator to function properly.

The size of the reagent holding openings is preferred to be made as small as possible in order to make the sample chamber of the bilirubin sensor as short as possible in order to minimize the volume of sample required for each test measurement. The three reagent holding/electrode openings 32, 34 and 36 are aligned with each other and are spaced about 0.02 in. (0.508 mm) to about 0.05 in. (1.27 mm) from each other. The circular reagent holding openings are for illustrative purposes only. It should be understood that the shape of the reagent holding openings and the distance between each of the electrodes is not critical. In fact, the reagent holding openings may differ in surface area from each other so long as the ratio of the surface areas remain substantially constant from one sensor to another.

The positional arrangement of the working, substrate and reference electrodes in the channel is not critical for obtaining usable results from the bilirubin sensor. The possible electrode arrangements within the sample fluid channel may be W-S-R, W-R-S, R-W-S, S-W-R, S-R-W, or R-S-W, with the arrangement listed as the electrodes would appear from the sample inlet 18 of laminated body 12 to the vent opening 52. The preferred position was found to be W-R-S; that is, as the fluid sample enters sampling end 14 of laminated body 12, the fluid sample would cover the working electrode first, then the reference electrode, and then the substrate electrode.

The three electrodes are each in electric contact with separate conductive paths. The separate conductive paths terminate and are exposed for making an electrical connection to a reading device on the end opposite from the sample inlet 18 of laminated body 12.

Channel forming layer 40 has a channel notch 42 located at the fluid sampling end 14. The length of channel notch 42 is such that when channel forming layer 40 is laminated to reagent holding layer 30, electrode areas W, R and S are within the space defined by channel notch 42. The length, width and thickness of the channel notch 42 define the capillary chamber volume.

Channel forming layer 40 is made of a plastic material, preferably a medical grade, double-sided pressure-sensitive adhesive tape available from Adhesive Research, Inc., of Glen Rock, Pa. or Global Instrument Corporation (Taiwan). The thickness of the tape is preferably in the range of about 0.001 in. (0.025 mm) to about 0.010 in. (0.25 mm). Channel notch 42 can be made with a laser or by die-cutting (the preferred method). The length of channel notch 42 is about 0.200 in. (5.08 mm) to about 0.250 in. (6.35 mm), the width is about 0.05 in. (1.27 mm) to about 0.07 in. (1.778 mm) and the thickness is about 0.0035 (0.089 mm) to about 0.0065 in. (0.165 mm). It should be understood that the thickness and the size of channel notch 42 are not critical.

Cover 50, which is laminated to channel forming layer 40, has vent opening 52 spaced from fluid sampling end 14 of bilirubin sensor 10 to ensure that the sample in the sample chamber 17 will completely cover electrode areas W, R and S. Vent opening 52 is positioned in cover 50 so that it will expose a portion of and partially overlay channel notch 42 at or near the closed end of the channel notch 42. Vent opening 52 may be any shape but is illustrated as a rectangle having dimensions of about 0.08 in. (2 mm) by about 0.035 in. (0.9 mm). The preferred material for cover 50 is a polyester film. In order to facilitate capillary action of the sample fluid within the sample chamber, it is desirable for the polyester film to have a highly hydrophilic surface on that portion of the polyester film that forms the capillary chamber. Transparency films from 3M or from GIC can be used. Cover 50 may optionally include an inlet notch 54 to prevent an inadvertent occlusion of sample inlet 18 (which can prevent the proper transfer of the sample fluid to the electrodes) when applying a blood sample to sample chamber 17.

FIG. 3 illustrates a 3-layer bilirubin sensor 10'. Like the 4-layer embodiment, bilirubin sensor 10' has a laminated body 12, a fluid sampling end 14, an electrical contact end 16, and a vent opening 52. Fluid sampling end 14 includes a sample chamber 17 between a sample inlet 18 and vent opening 52. Electrical contact end 16 has three discrete conductive contacts 16a, 16b and 16c.

As can be seen from FIG. 4, laminated body 12 includes a base layer 20, a channel forming layer 40, and a cover 50. As noted earlier, all layers of laminated body 12 are made of a dielectric material, preferably plastic. Unlike the 4-layer embodiment, there is no separate reagent holding layer in the 3-layer embodiment. Channel forming layer 40 also delineates the area in which a pre-determined amount of reagent mixtures are disposed onto the conductive paths as three distinct drops or droplets on the working, substrate and reference electrodes, respectively.

Turning now to FIG. 5, there is illustrated another embodiment of the present invention showing a bilirubin sensor 500. Bilirubin sensor 500 has a laminated body 512, a sample receiving well 514 and an electrical contact end 516. Laminated body 512 has a base layer 520 and a cover 550. Cover 550 has a sample opening 552 that forms, when combined with base layer 520, sample receiving well 514. Base layer 520 has at least three electrical paths 522, 524 and 526, which have a first portion exposed at electrical contact end 516 for connection to a meter device (not shown) and a second portion exposed by sample receiving well 514.

The second portion of electrical paths 522, 524 and 526 exposed by sample receiving well 514 create at least a working electrode W, a substrate electrode S and at least a reference/counter electrode R. A first reagent mixture 560 contains at least a polymer binder and a chemically oxidizing reagent and is disposed on the working electrode W. A second reagent mixture 562 contains a polymer binder, a chemically oxidizing reagent and a chemical agent that consumes bilirubin and is disposed on the substrate electrode S. The reference/counter electrode R may contain any reference material previously disclosed. In this embodiment of the present invention, sample receiving well 514 serves as both the sample inlet and the sample chamber for receiving a fluid sample such as blood for the determination of bilirubin.

It should be understood that the conduit paths in any of the embodiments disclosed herein may be made from any non-corroding metal. Carbon deposits such as for example carbon paste or carbon ink may also be used as the conduit paths, all as is well known by those of ordinary skill in the art.

Chemical Reagents

Enzyme

The bilirubin sensor of the present invention includes at least a chemical agent in the substrate electrode S that consumes bilirubin. The chemical agent is preferably a bilirubin sensitive enzyme, and, more preferably, bilirubin oxidase, which can selectively react with bilirubin in the sample fluid. The substrate electrode is essential in the present invention for making an accurate determination of the concentration of bilirubin in a body fluid. As previously explained, the use of such a substrate electrode helps to distinguish the oxidation current caused by bilirubin from the oxidation current caused by other oxidizable species in the sample fluid. A commercially available bilirubin oxidase from Sigma Chemical Company, St. Louis, Mo., or from Amono, Japan is used for the preparation of the bilirubin substrate electrode. The concentration of bilirubin oxidase in the reagent mixture is in the range of about 10 units/ml to 90 units/ml.

Chemically Oxidizing Reagents

Chemically oxidizing reagents such as redox mediators may optionally be included in the bilirubin sensor. It is preferable to use a redox mediator in its oxidized form. It is also desirable that the reduced form of the mediator is capable of being oxidized electrochemically at the electrode surface at the applied potential. It is further desirable that the mediator is stable in the reagent matrix. When used in a reference electrode, it is still further desirable that the mediator can make the reference electrode function properly. The redox mediator can be selected from, but not limited to, various metal compounds and organic redox compounds. Examples of acceptable redox mediators include potassium (or sodium) ferricyanide, ferrocene and its derivatives, cupric compounds, nitrite compounds, ruthenium compounds such as hexaammineruthenium(III) chloride and its derivatives, and osmium complexes. The preferred mediator is potassium ferricyanide. The concentration of potassium ferricyanide in the reagent mixture is preferably about 1% to about 15% (w/w) of the reagent mixture.

Because the use of a chemically oxidizing reagent is optional, the redox mediator is not a necessary ingredient in the reagent matrix to be disposed in the working electrode and substrate electrode wells of the bilirubin sensor. In this embodiment, the working electrode is only loaded with a polymer binder and, preferably, with a bulking reagent, a surfactant and a buffer. The substrate electrode is loaded with the same chemicals as the working electrode but with the addition of a chemical agent that consumes bilirubin. The preferred chemical agent is bilirubin oxidase. A higher positive potential (e.g., 0.8 V) is needed to be applied between the working/substrate electrodes and the reference electrode when no chemically oxidizing reagent is included. All of the reductants including bilirubin in the sample will contribute the oxidation current response signal when the higher positive potential is applied at the working electrode. Meanwhile, at the substrate electrode, bilirubin will be consumed by the bilirubin oxidase. Consequently, the oxidation current response will be from all of the reductants in the sample fluid except bilirubin. The differential current response between the working electrode and the substrate electrode is related to the concentration of bilirubin.

Polymers

The polymer used as the binder in the reagent matrix should be sufficiently water-soluble and should also be capable of stabilizing and binding all other chemicals in the reagent to the conductive surface layer in the electrode area. Suitable polymers include, but are not limited to, polyethylene oxide (PEO), polyvinyl pyrolidone, starch, methylcellulose, polyvinyl alcohol (PVA), carboxy methyl cellulose (CMC), and polyamino acids. The reagent binder may be a single polymer or a combination of polymers. The preferred binder in the present invention is a combination of polyethylene oxide (PEO) and methylcellulose. PEO's molecular weight ranges from thousands to millions and is available from Scientific Polymer Products, NY, USA. The concentration of PEO in the reagent mixture is preferably about 0.04% (W/W) to about 2%. Methylcellulose, which is available under the brand name of Methocel 60 HG (Cat. No. 64655, Fluka Chemicals, Milwaukee, Wis., USA) has a concentration in the reagent mixture preferably in the range of about 0.02% (w/w) to about 5%.

Surfactants

The surfactant may be optionally included in the reagent mixture to facilitate dispensing of the reagent mixture into the electrode areas. The surfactant also helps in quickly dissolving the dry chemical reagents when a sample fluid enters the sample channel of the bilirubin sensor. The amount and type of surfactant is selected to assure the previously mentioned functions and to avoid a denaturing effect on the enzymes. Surfactants can be selected from, but are not limited to, various anionic, cationic, non-ionic, and zwitterionic detergents. Examples of acceptable surfactants are polyoxyethylene ether, Tween 20, sodium cholate hydrate, hexadecylpyridinium cholide monohydrate and CHAPs. The preferred surfactant is a polyoxyethylene ether. More preferably, it is t-octylphenoxypolyethoxyethanol and is available under the brand name Triton X-100. The concentration of Triton X-100 in the reagent mixture is preferably about 0.01% (w/w) to about 2%.

Buffer

Optionally, a buffer may be present along with a redox mediator in dried form in the sensor strip of the present invention. The buffer is present in a sufficient amount so as to substantially maintain the pH of the reagent mixtures. Examples of suitable buffers include citric acid, phosphates, Tris, and the like. In the present invention, the pH of the buffer is preferably in the range from about 5.0 to about 8.5.

Bulking Reagent

An optional bulking agent that is water soluble and an inactive ingredient is preferably added into the reagent mixture. The use of a bulking agent is advantageous when an electrode forming layer is used to contain the reagent matrix such that the electrode openings in the electrode forming layer will not trap bubbles when a sample fluid fills the capillary channel. Various sugars such as, for example, trehalose, galactose, glucose, sucrose, lactose, mannitol, mannose, fructose, sucrose, lactose, lactitol, sorbitol, xylitol, nicotinamide, maltose, and the like, can be added into the reagent mixture as long as they do not react with other ingredients and are inactive at the electrode surface. The bulking agent can be one chemical or a combination of chemicals. The amount of bulking agent in the reagent mixture is in the range from about 1% to about 15% (w/w).

Accordingly, the preferred reagent mixture (referred to below as "reagent mixture 1") used for the bilirubin working electrode (W) and reference electrode (R) contains Methocel 60 HG, polyethylene oxide, potassium ferricyanide, Triton X-100, bulking agents, and Tris buffer (pH 8). The preferred reagent mixture (referred to below as "reagent mixture 2") used for the substrate electrode (S) contains Methocel 60 HG, polyethylene oxide, potassium ferricyanide, Triton X-100, bulking agents, bilirubin oxidase, and Tris buffer (pH 8).

Preparation of the Reagent Mixtures

Reagent mixture 1 is preferably prepared in two steps, although it can be prepared in one step:

Step 1: Into Tris buffer (pH 8), add Methocel 60 HG, polyethylene oxide, methylcellulose, bulking agent, and Triton X-100. Stir the solution until dissolved using a magnetic stirrer.

Step 2: Into the above solution, add potassium ferricyanide. Stir the solution until dissolved. The resulting solution is ready for dispensing.

Reagent mixture 2 is prepared in two steps:

Step 1: Into Tris buffer (pH 8), add Methocel 60 HG, polyethylene oxide, methylcellulose, bulking agent, and Triton X-100. Stir the solution until dissolved using a magnetic stirrer.

Step 2: Into the above solution, add potassium ferricyanide and bilirubin oxidase. Stir the solution until dissolved. The resulting solution is ready for dispensing.

Sensor Construction

Assembly of the various embodiments of the present invention is relatively straightforward. Generally for the 4-layer configuration, the base layer and reagent holding layer are laminated to each other followed by dispensing the appropriate reagent mixture into each of the reagent holding openings. After drying the reagent mixture, the channel forming layer is laminated onto the reagent holding layer and the cover is then laminated onto the channel forming layer. For the 3-layer construction, the base layer and the channel forming layer are laminated to each other followed by dispensing the appropriate reagent mixture as distinct drops/droplets into the U-shaped channel onto their respective conductive surface areas. After drying the reagent mixture, the cover is then laminated onto the channel forming layer.

More particularly, a piece of a gold polyester film is cut to shape as illustrated in FIG. 2, forming base layer 20 of sensor 10. A laser (previously disclosed) is used to score the gold polyester film. As illustrated in FIG. 2, the film is scored by the laser such that three electrodes at sample fluid end 14 and three contact points 22, 24 and 26 are formed at electrical contact end 16. The scoring line is very thin but sufficient to create three separate electrical paths. A scoring line 28 may optionally be made, but is not necessary, along the outer edge of base layer 20 to avoid potential static problems which could cause a noisy signal from the finished sensor 10.

A piece of one-sided adhesive tape is then cut to size and shape, forming reagent holding layer 30 so that it will cover a major portion of conductive layer 21 of base layer 20 except for exposing a small electrical contact area illustrated in FIG. 1 by reference number 16.

Before attaching reagent holding layer 30 to base layer 20, three circular openings 32, 34 and 36 of substantially equal size are punched by laser, or by mechanical means such as a die-punch assembly, creating electrode openings 32, 34 and 36 in reagent holding layer 30. The preferred hole size for openings 32, 34 and 36 has a typical diameter of about 0.030 in. (0.76 mm). As illustrated in FIG. 2, electrode openings 32, 34 and 36 are aligned with each other and have a spacing of about 0.020 in. (0.508 mm) to about 0.050 in. (1.27 mm) between adjacent openings. The circular openings are for illustrative purposes only. It should be understood that the shape and size of the openings is not critical. The circular openings do not have to be substantially equal in size so long as the ratio of the surface areas remains substantially constant. As stated previously, the preferred arrangement of the electrodes formed in openings 32, 34 and 36 is W (working electrode), R (reference electrode) and S (substrate electrode). Reagent holding layer 30 is then attached to base layer 20 in such a way as to define the electrode wells W, R and S.

Approximately 0.05 to 0.09 microliters (μL) of reagent mixture 1 is dispensed into the working and reference electrode areas W and R. As described above, reagent mixture 1 is preferably a mixture of a bulking agent, a polymer binder, a surfactant, a redox mediator and a buffer. Similarly, approximately 0.05 to 0.09 μL of reagent mixture 2 is dispersed into substrate electrode area S.

After dispensing the reagents in their respective electrode areas, the reagents are dried at a temperature in the range of about room temperature to about 60° C. The length of time required to dry the reagents is dependent on the temperature at which the drying process is performed.

After drying, a piece of double-sided tape available from Adhesive Research or GIC is fashioned into chamber forming layer 40 containing U-shaped channel 42. Chamber forming layer 40 is then layered onto reagent holding layer 30. As mentioned earlier, this chamber forming layer 40 serves as a spacer and defines the size of sample chamber 17.

A piece of a transparency film available from 3M or from GIC is fashioned into top layer 50. A vent opening 52 is made using the laser previously mentioned or by means of a die-punch. Vent opening 52 is located approximately 0.180 in. (4.57 mm) from fluid entrance 54. Top layer 50 is aligned and layered onto chamber forming layer 40 to complete the assembly of bilirubin sensor 10, as illustrated in FIG. 1.

Testing the Bilirubin Sensor

When a fluid sample is applied to a single strip of the present invention, the fluid sample enters the channel through the sampling inlet 18 and flows over W, R and S and stops at the threshold of the vent opening 52.

Chronoamperometry (i-t curve) was used for measurement of the current response of the bilirubin sensor using an Electrochemical Analyzer (Model 812, CH Instruments, Austin, Tex., USA). Once a blood sample enters the sensor, a potential of 0.3 to 0.5 volts is applied across the working/substrate electrodes and the reference electrode on those sensors that use a chemically oxidizing reagent in the reagent matrix. For sensors constructed with a reagent matrix that does not contain a chemically oxidizing reagent (e.g., redox mediator), a potential of about 0.8 volts is used. The bilirubin concentration of the same blood sample is measured with a Dade Behring Dimension® RxL Clinical Chemistry System.

The above described embodiments are based on amperometric analyses. Those skilled in the art, however, will recognize that a sensor of the invention may also utilize coulometric, potentiometric, voltammetric, and other electrochemical techniques to determine the concentration of an analyte in a sample.

The following examples illustrate the unique features of the present invention.

EXAMPLE 1

Determination of Bilirubin Concentration Using a Chemical Matrix Containing Ferricyanide and Bilirubin Oxidase Blood samples with different bilirubin concentrations were tested with the bilirubin sensors of the present invention using the above-described reagent formulations. Table 1 shows the corrected current response in nanoamps in a blood sample with varying levels of bilirubin. The corrected current response means the differential current response between the working electrode and the substrate electrode.

TABLE 1

| Linearity | |
|---|---|
| Bilirubin concentration (mg/dL) | Corrected current response (nA) |
| 0.5 | 32.9 |
| 1.7 | 34.6 |
| 3.1 | 37.3 |
| 4.5 | 38.8 |
| 7.0 | 43.8 |
| 10.5 | 48.4 |
| 13.5 | 54.2 |
| 20.6 | 66.0 |
| 25.0 | 71.9 |

Figure 6:
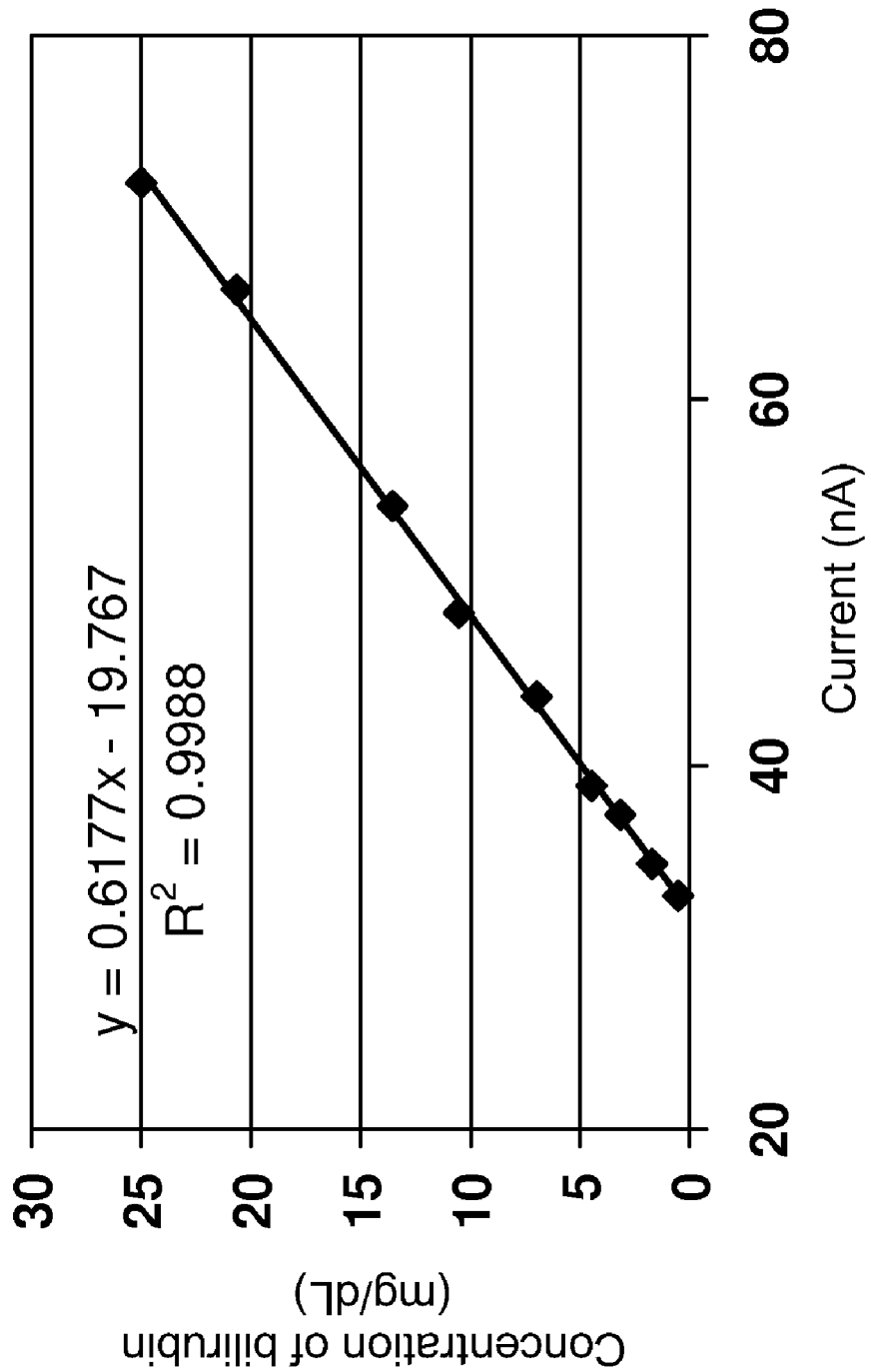
FIG. 6 illustrates the correlation between the current response of the bilirubin sensor of the present invention to bilirubin concentration using ferricyanide and bilirubin oxidase in the chemical matrix.

A graphical illustration of the test data is shown in FIG. 6. The test results demonstrate that the sensor of the present invention has a linear response (current response vs. bilirubin concentration) over a bilirubin concentration range from 0 to 25 mg/dL.

EXAMPLE 2

Precision of Bilirubin Sensor

The precision of the bilirubin sensor of present invention was investigated with two levels of bilirubin (2.3 mg/dL and 8.8 mg/dL) in blood samples. Table 2 shows the precision of the response of the bilirubin sensor of the present invention. A total of 10 measurements were made on each level of bilirubin blood sample.

TABLE 2

| Precision | | |
|---|---|---|
| | Results | |
| Measurement No | mg/dL | mg/dL |
| 1 | 2.2 | 9.1 |
| 2 | 2.1 | 8.8 |
| 3 | 2 | 9.2 |
| 4 | 2.5 | 9 |
| 5 | 2.5 | 9.2 |
| 6 | 2.3 | 8.9 |
| 7 | 2.2 | 9.1 |
| 8 | 2 | 8.8 |
| 9 | 2.2 | 9.3 |
| 10 | 2.2 | 9 |

TABLE 2-continued

Precision

| Measurement No | Results mg/dL | mg/dL |
|---|---|---|
| Mean | 2.22 | 9.04 |
| CV (%) | 7.9 | 1.9 |

Figure 7:
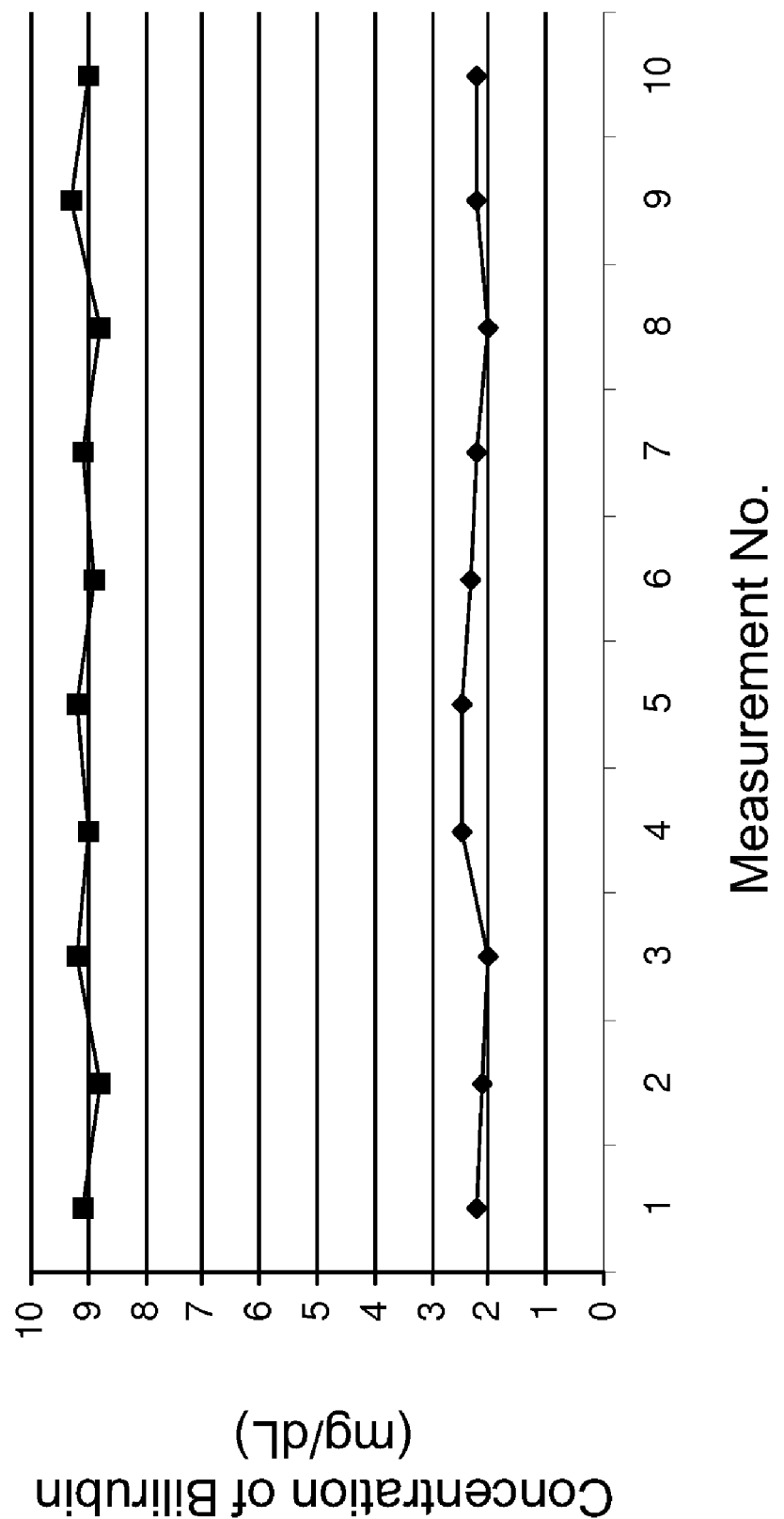
FIG. 7 illustrates the precision of the bilirubin sensor of the present invention at two different bilirubin concentrations.

A graphical illustration of the test data is shown in FIG. 7.

EXAMPLE 3

Determination of Bilirubin Concentration Using a Chemical Matrix Containing Hexaammineruthenium (III) Chloride and Bilirubin Oxidase Blood samples with different bilirubin concentrations were tested with the bilirubin sensors of the present invention with above reagent formulations using a different chemically oxidizing reagent. Table 3 shows the current response in nanoamps in a blood sample with varying levels of bilirubin.

TABLE 3

Linearity

| Bilirubin concentration (mg/dL) | Current response (nA) |
|---|---|
| 0.7 | 12.5 |
| 2.3 | 14.0 |
| 4.0 | 16.3 |
| 5.5 | 18.6 |
| 8.8 | 23.5 |
| 13.5 | 29.2 |
| 15.8 | 31.9 |
| 23.0 | 44.9 |

Figure 8:
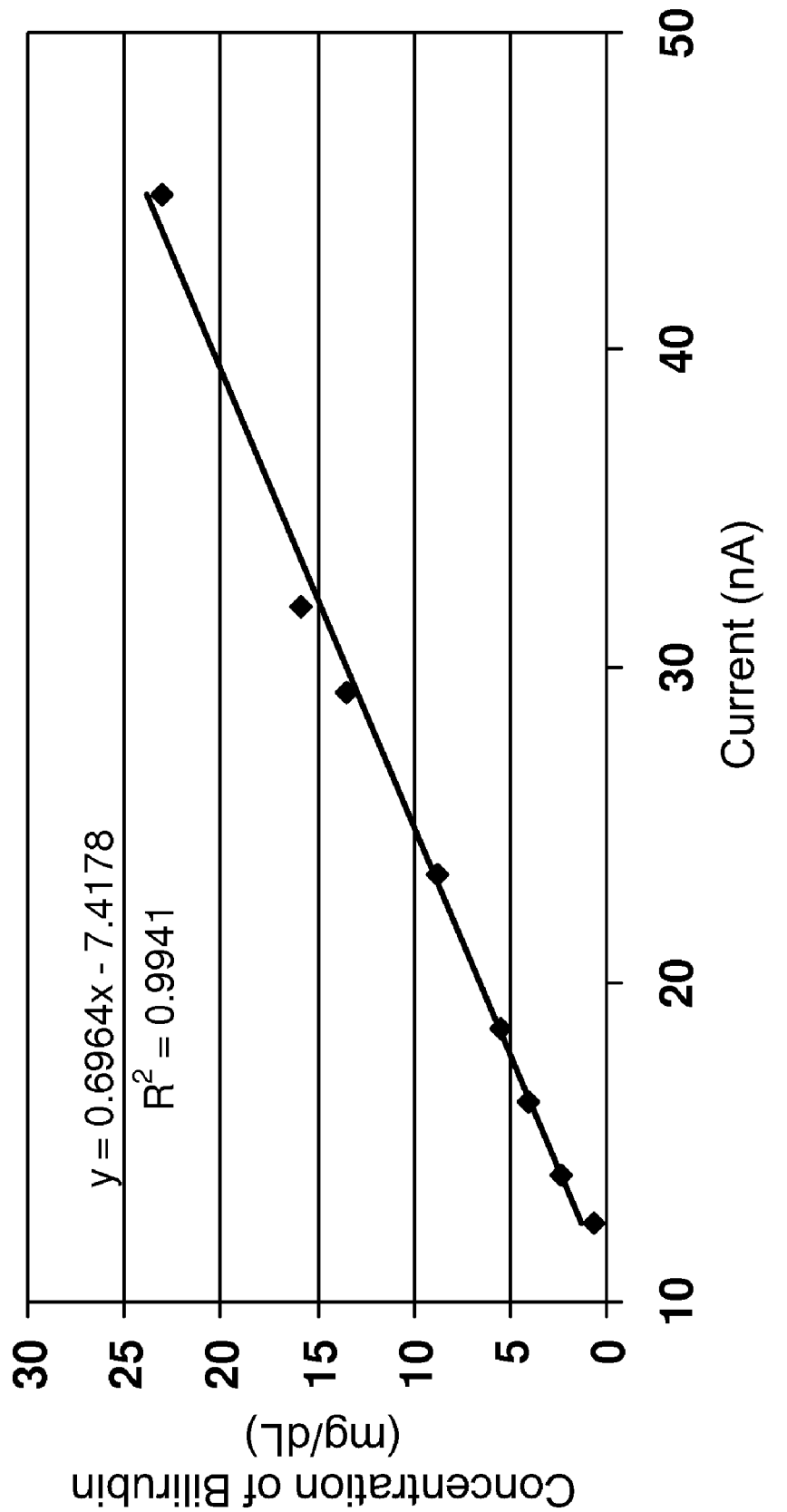
FIG. 8 illustrates the correlation between the current response of the bilirubin sensor of the present invention to bilirubin concentration using hexaamineruthenium (III) chloride and bilirubin oxidase in the chemical matrix.
Figure 9:
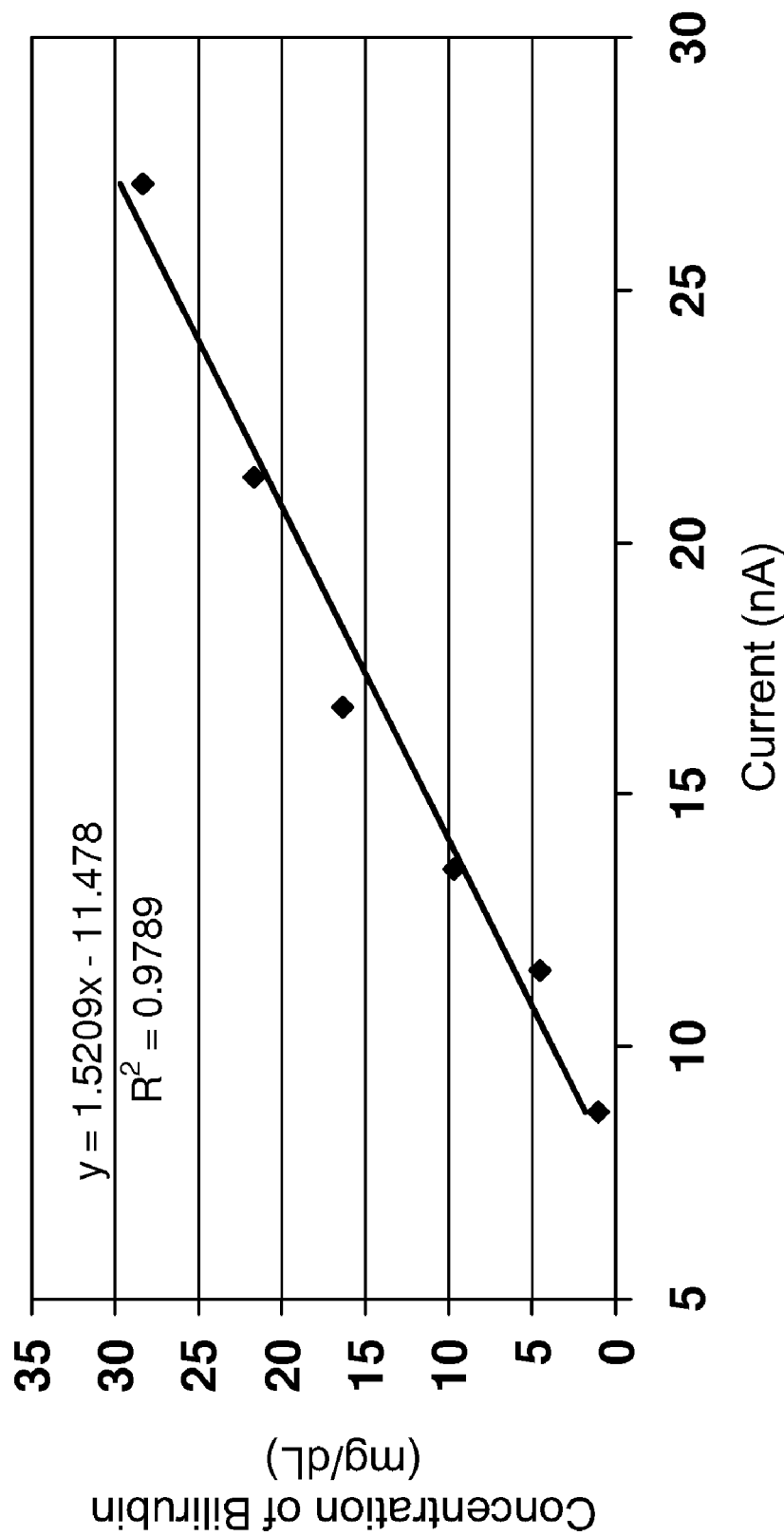
FIG. 9 illustrates the correlation between the current response of the bilirubin sensor of the present invention to bilirubin concentration using chemical matrix that does not include a chemically oxidizing reagent/redox mediator.

A graphical illustration of the test data is shown in FIG. 8. The test results demonstrate that the sensor of the present invention has a linear response (current response vs. bilirubin concentration) over a bilirubin concentration range from 0 to 23 mg/dL.

EXAMPLE 4

Determination of Bilirubin Concentration Using a Chemical Matrix that Does Not Contain a Chemically Oxidizing Reagent Blood sample with different bilirubin concentrations were tested with the bilirubin sensors of the present invention with above reagent formulations. Table 4 shows the current response in nanoamps in a blood sample with varying levels of bilirubin.

TABLE 4

Linearity

| Bilirubin concentration (mg/dL) | Current response (nA) |
|---|---|
| 1.0 | 8.7 |
| 4.5 | 11.5 |
| 9.7 | 13.5 |
| 16.3 | 16.7 |

TABLE 4-continued

Linearity

| Bilirubin concentration (mg/dL) | Current response (nA) |
|---|---|
| 21.6 | 21.3 |
| 28.3 | 27.1 |

A graphical illustration of the test data is shown in FIG. 8. The test results demonstrate that the sensor of the present invention has a linear response (current response vs. bilirubin concentration) over a bilirubin concentration range from 0 to 28 mg/dL.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A bilirubin sensor comprising:
a working electrode with a first chemical matrix disposed thereon, the first chemical matrix containing a binder, wherein the first chemical matrix is capable of oxidizing all oxidizable species in a fluid sample;
a substrate electrode with a second chemical matrix disposed thereon, the second chemical matrix containing a binder and a chemical agent that consumes bilirubin, wherein the second chemical matrix is capable of oxidizing all oxidizable species in the fluid sample except bilirubin;
a reference electrode;
a sample chamber containing the working electrode, the substrate electrode and the reference electrode;
means for applying a potential between the reference electrode and the working electrode to obtain a first current;
means for applying a potential between the reference electrode and the substrate electrode to obtain a second current;
means for correlating the first current to a concentration of all oxidizable species in the fluid sample and for correlating the second current to a concentration of all oxidizable species in the fluid sample except bilirubin;
means for subtracting the second current from the first current to obtain a current difference;
and means for correlating the current difference to a concentration of bilirubin in the fluid sample.

2. The bilirubin sensor of claim 1 wherein the chemical agent is an oxidoreductase of bilirubin.

3. The bilirubin sensor of claim 2 wherein the oxidoreductase of bilirubin is bilirubin oxidase.

4. The bilirubin sensor of claim 1 wherein the first chemical matrix and the second chemical matrix contains a chemically oxidizing reagent.

5. The bilirubin sensor of claim 4 wherein said chemically oxidizing reagent is a redox mediator.

6. The bilirubin sensor of claim 4 wherein the chemically oxidizing reagent is selected from the group consisting of potassium ferricyanide, sodium ferricyanide, ferrocene, ferrocene derivatives, cupric sulfate, hexaammineruthenium (III) chloride, hexaammineruthenium (III) chloride derivatives, and osmium complexes.

7. The bilirubin sensor of claim 1 wherein the bilirubin sensor is an amperometry-based sensor.

8. The bilirubin sensor of claim 1 wherein the first chemical matrix and the second chemical matrix includes one or more reagents selected from the group consisting of a bulking agent, a surfactant and a buffer.

9. The bilirubin sensor of claim 8 wherein the buffer has a pH in the range from about 5.0 to about 8.5.

10. The bilirubin sensor of claim 1 wherein the binder includes one or more chemical reagents selected from the group consisting of polyethylene oxide, polyvinyl pyrolidone, starch, methylcellulose, polyvinyl alcohol, carboxy methyl cellulose, and polyamino acids.

11. A bilirubin sensor comprising:
a working electrode with a first chemical matrix disposed thereon, the first chemical matrix containing a whole blood filtering component, wherein the first chemical matrix is capable of oxidizing all oxidizable species in a fluid sample;
a substrate electrode with a second chemical matrix disposed thereon, the second chemical matrix containing a whole blood filtering component and a chemical agent that consumes bilirubin, wherein the second chemical matrix is capable of oxidizing all oxidizable species in the fluid sample except bilirubin;
a reference electrode;
a sample chamber containing the working electrode, the substrate electrode and the reference electrode;
means for applying a potential between the reference electrode and the working electrode to obtain a first current;
means for applying a potential between the reference electrode and the substrate electrode to obtain a second current;
means for correlating the first current to a concentration of all oxidizable species in the fluid sample and for correlating the second current to a concentration of all oxidizable species in the fluid sample except bilirubin;
means for subtracting the second current from the first current to obtain a current difference;
and means for correlating the current difference to a concentration of bilirubin in the fluid sample.

12. The bilirubin sensor of claim 11 wherein the chemical agent is an oxidoreductase of bilirubin.

13. The bilirubin sensor of claim 12 wherein the oxidoreductase of bilirubin is bilirubin oxidase.

14. The bilirubin sensor of claim 11 wherein the first chemical matrix and the second chemical matrix contains a chemically oxidizing reagent.

15. The bilirubin sensor of claim 14 wherein said chemically oxidizing reagent is a redox mediator.

16. The bilirubin sensor of claim 14 wherein the chemically oxidizing reagent is selected from the group consisting of potassium ferricyanide, sodium ferricyanide, ferrocene, ferrocene derivatives, cupric sulfate, hexaamineruthenium (III) chloride, hexaamineruthenium (III) chloride derivatives, and osmium complexes.

17. The bilirubin sensor of claim 11 wherein the bilirubin sensor is an amperometry-based sensor.

18. The bilirubin sensor of claim 11 wherein the first chemical matrix and the second chemical matrix includes one or more reagents selected from the group consisting of a bulking agent, a surfactant and a buffer.

19. The bilirubin sensor of claim 18 wherein the buffer has a pH in the range from about 5.0 to about 8.5.

20. A method of measuring bilirubin in a fluid sample comprising the steps of:
disposing the fluid sample into a sample chamber of a bilirubin sensor;
applying a potential between a reference electrode and a working electrode in the sample chamber, wherein the working electrode has a first chemical matrix disposed thereon that contains a binder and that serves to oxidize all oxidizable species in the fluid sample;
measuring a first current generated between the working electrode and the reference electrode, wherein the first current is correlated to a concentration of all oxidizable species in the fluid sample;
applying a potential between the reference electrode and a substrate electrode in the sample chamber, wherein the substrate electrode has a second chemical matrix disposed thereon that contains a binder and a chemical agent that consumes bilirubin so as to oxidize all oxidizable species in the fluid sample except bilirubin;
measuring a second current generated between the reference electrode and the substrate electrode, wherein the second current is correlated to a concentration of all oxidizable species in the fluid sample except bilirubin;
subtracting the second current from the first current and obtaining a current difference; and
correlating the current difference to a concentration of bilirubin in the fluid sample.

21. The method of claim 20 further comprising:
measuring a resistance value of the fluid sample between the reference electrode and one of the working electrode, the substrate electrode, or both;
applying the resistance value to a first equation and determining the hematocrit level of the fluid sample from the first equation; and
calculating a corrected concentration of bilirubin using a second equation to correct for the presence of hematocrit in the fluid sample.

22. The method of claim 20 wherein the potential applying steps include applying a potential of about 0.800 volts.

23. The method of claim 20 wherein the potential applying steps include applying a potential of about 0.350 volts when the first chemical matrix and the second chemical matrix contains a chemically oxidizing reagent.

24. The method of claim 20 further comprising triggering the current measuring step when the fluid sample contacts the working electrode, the substrate electrode and the reference electrode.

25. The method of claim 20 further comprising:
measuring a resistance value of the fluid sample between the reference electrode and one of the working electrode, the substrate electrode, or both; and
applying the resistance value to a derived algorithm to correct for the presence of hematocrit in the fluid sample.

* * * * *